(12) United States Patent
Jacobson

(10) Patent No.: US 6,667,421 B2
(45) Date of Patent: Dec. 23, 2003

(54) HYDROGEN REDUCTION OF SULFONYL CHLORIDES TO THIOLS

(75) Inventor: Stephen E. Jacobson, Princeton, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/220,445

(22) PCT Filed: Feb. 26, 2001

(86) PCT No.: PCT/US01/06129

§ 371 (c)(1), (2), (4) Date: Aug. 28, 2002

(87) PCT Pub. No.: WO01/66517

PCT Pub. Date: Sep. 13, 2001

(65) Prior Publication Data

US 2003/0055290 A1 Mar. 20, 2003

Related U.S. Application Data

(60) Provisional application No. 60/186,902, filed on Mar. 3, 2000.

(51) Int. Cl.$^7$ .................. C07D 261/00; C07D 263/00; C07C 319/00
(52) U.S. Cl. .......... 568/68; 549/466; 548/243; 568/67
(58) Field of Search ............... 568/61, 67, 68; 546/290; 549/429, 462, 466; 548/146, 182, 215, 225, 243

(56) References Cited

U.S. PATENT DOCUMENTS

| | | | | |
|---|---|---|---|---|
| 2,792,422 A | * | 5/1957 | Harris et al. | 568/68 |
| 3,326,981 A | * | 6/1967 | Levy et al. | 568/64 |
| 4,006,186 A | * | 2/1977 | Engels et al. | 564/440 |
| 4,209,469 A | | 6/1980 | Thies et al. | |
| 4,725,604 A | * | 2/1988 | Hageman et al. | 514/324 |
| 4,816,176 A | * | 3/1989 | Lund et al. | 510/409 |
| 4,948,827 A | * | 8/1990 | Christidis | 524/392 |

OTHER PUBLICATIONS

CA:114:184896 abs of Chemical Industries 1990 40(catal, Org reaction) 189–96 by Mylroie et al 1990.*

CA:105:237622 abs of Sciences de la Terre 25(3–4) pp 307–21 by Montanari et al 1986.*

V.L. Mylroie et al: Chem. Ind., vol. 40, 1990, pp. 189–196 XP001001149.

* cited by examiner

Primary Examiner—Jean F. Vollano

(57) ABSTRACT

This invention relates to a process for the production of an aryl thiol, which comprises hydrogenating an aryl sulfonyl chloride in a solvent in the presence of a palladium catalyst and a base whose conjugate acid has a $pK_a$ of about 2 or greater, wherein the base is selected from the group consisting of ionic bases soluble in water and tertiary amines soluble in the solvent, the tertiary amines not having a methyl group attached to the amine nitrogen.

15 Claims, No Drawings

HYDROGEN REDUCTION OF SULFONYL CHLORIDES TO THIOLS

This application is a 35 U.S.C. 371 national stage application of International Application PCT/US01/06129, filed Feb. 26, 2001, which claims benefit of U.S. Provisional Application No. 60/186,902, filed Mar. 3, 2000.

BACKGROUND OF THE INVENTION

Aryl thiols are useful products and intermediates for the preparation of chemical derivatives useful in agricultural, pharmaceutical, photographic, coloration, rubber, plastics, metal finishing, corrosion protection, and other fields. One of the most important methods for the production of aryl thiols is by the reduction of the more readily produced aryl sulfonyl chlorides.

Many reduction processes have been employed, such as the use of zinc and acetic or sulfuric acid, or zinc plus red phosphorus and iodine. These processes lead to the generation of large amounts of harmful metal salts to be disposed of. Sulfonyl chlorides can also be reduced directly with pressurized hydrogen using certain metal sulfide catalysts such as cobalt, nickel, tungsten, molybdenum or iron sulfides. In these processes large amounts of catalysts, as much as 5% to 15% by weight relative to the reactant, are required.

Processes have also been proposed for the reduction of aryl sulfonyl chlorides to the corresponding thiols using pressurized hydrogen where the catalyst is a noble metal such as platinum or palladium. For example, U.S. Pat. No. 4,209,469 discloses a process for the production of an aryl thiol by hydrogenating the aryl sulfonyl chloride in a protic or aprotic solvent in the presence of a platinum catalyst at a temperature of 100 to 180° C. and a pressure of 2 to 140 bar (200–14000 kPa). A highly acidic byproduct, hydrogen chloride, is formed during the reaction. After the hydrogenation is complete, 2.5 moles of sodium hydroxide are added per mole of sulfonyl chloride to neutralize the HCl and convert the thiol to the sodium salt. However, carrying out the reduction step under strongly acidic conditions and high temperatures causes unacceptable corrosion of even expensive nickel-based alloys.

A process intended to overcome this corrosion problem is disclosed in "Reduction of Sulfonyl Chlorides to Thiols", V. L. Mylroie and J. K. Doles, *Catalysis of Organic Reactions*, Blackburn ed., Marcel Dekker, Inc., NY, 1990. They used a palladium on carbon catalyst for the hydrogen reduction step in the presence of a solvent such as tetrahydrofuran, along with one of several alkaline materials to simultaneously neutralize the hydrogen chloride byproduct as it forms and minimize corrosion. A strong base tested, N,N-dimethylbenzeneamine, was reported to perform poorly and little thiol was produced. A strongly basic Amberlite® resin tested was reported to produce disulfides as well. This lowered the yield of thiol and/or required that a second process using Raney® cobalt catalyst be used to convert disulfides to the thiols. Nevertheless, they obtained relatively good yields of thiol when using N,N-dimethylacetamide as the base. They concluded from these experiments that it was necessary to use a mild base such as N,N-dimethylacetamide rather than a strong base for the neutralization of hydrogen chloride during the hydrogenation step.

However, a mild base such as N,N-dimethylacetamide does not adequately prevent corrosion from a very strong acid such as hydrogen chloride. In tests of the above process, significant corrosion was observed using N,N-dimethylacetamide for neutralization of the hydrogen chloride, even when an expensive nickel-based alloy such as Hastelloy® C was employed. Another disadvantage of the above process is that a large amount of N,N-dimethylacetamide is required for neutralization, and the recovery of the N,N-dimethylacetamide from the product solution is difficult. There is a need for a process to convert aryl sulfonyl chlorides to aryl thiols using a hydrogen reduction process with a noble metal catalyst, but without these disadvantages.

SUMMARY OF THE INVENTION

This invention relates to a process for the production of an aryl thiol, which comprises hydrogenating an aryl sulfonyl chloride with hydrogen in a solvent in the presence of (i) a catalyst comprising palladium and (ii) an effective amount of a base whose conjugate acid has a $pK_a$ of about 2 or greater, wherein the base is selected from the group consisting of ionic bases soluble in water and tertiary amines soluble in the solvent, the tertiary amines not having a methyl group attached to the amine nitrogen. Preferably the palladium catalyst further comprises from about 5% to about 20% by weight of tin relative to the palladium, more preferably about 8% to about 12%.

DETAILS OF THE INVENTION

The process of the present invention can be illustrated by the following equation, wherein Ar represents an unsubstituted or substituted aryl derivative and —SO$_2$Cl is bonded directly to a carbon atom in an aromatic ring system moiety of the aryl group:

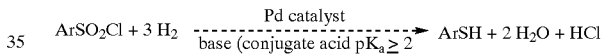

$$ArSO_2Cl + 3\,H_2 \xrightarrow[\text{base (conjugate acid } pK_a \geq 2)]{\text{Pd catalyst}} ArSH + 2\,H_2O + HCl$$

The aryl group of the aryl sulfonyl chlorides useful in the present invention includes unsubstituted and substituted, mononuclear and polynuclear, aromatic, carbocyclic and heterocyclic, ring systems. As used herein, the term "aryl", used either alone or in compound words such as "aryl sulfonyl", "alkylaryl" or "aryloxy" denotes a radical derived from an aromatic ring system. The term "aromatic ring system" denotes fully unsaturated carbocycles and heterocycles in which the polycyclic ring system is aromatic (where aromatic indicates that the Hückel rule is satisfied for the ring system). The term "aromatic carbocyclic ring system" includes fully aromatic carbocycles and carbocycles in which at least one ring of a polycyclic ring system is aromatic (where aromatic indicates that the Hückel rule is satisfied). The term "aromatic heterocyclic ring system" include fully aromatic heterocycles and heterocycles in which at least one ring of a polycyclic ring system is aromatic (where aromatic indicates that the Hückel rule is satisfied). Examples of suitable aryl groups are groups containing aromatic and heteroaromatic five and six-membered rings such as benzene, thiophene, pyridine, pyridazine, pyrazine, pyrimidine, triazine, triazole, pyrrole, imidazole, pyrazole, furan, oxazole, isoxazole, thiazole, thiadiazole, oxathiazole and polycyclic rings comprising combinations of the mononuclear aromatic structures, such as naphthalene, benzo[b]thiophene, benzofuran, quinoline, isoquinoline, quinoxaline, indole, isoindole, naphthyridine, indazole, benzopyrrole, benzotriazole, benzimidazole, benzoxazole, benzothiadiazole, and benzisothiazole. Additionally, polynuclear structures may be included, where one of the rings is aromatic and the other saturated. Examples include such compounds as 1,2,3,4-tetrahydronapthalene, dihydroindole, dihydroisoindole and dihydrobenzopyran. An enormous variety of aryl ring systems suitable for the process of the present invention and methods for preparation of these aryl ring systems are well known in the art. For extensive reviews see: *Comprehensive Organic Chemistry*, D. Barton and W. D. Ollis eds., Pergamon Press, NY, 1979, Volumes 1–6; *Comprehensive Heterocyclic Chemistry*, A. R. Katritzky and C. W. Rees eds., Pergamon Press, NY, 1984, Volumes 1–8; *Comprehensive Heterocyclic Chemistry II*, A. R. Katritzky, C. W. Rees and E. F. V. Scriven eds., Pergamon Press, NY, 1996, Volumes 1A-11; and the references cited therein.

Suitable substituents on the aryl group are those moieties that are not reducible under the palladium-catalyzed hydrogenation reaction conditions, which are understood by one skilled in the art. For a review of the susceptibility of organic groups to hydrogenation, see P. N. Rylander, *Catalytic Hydrogenation in Organic Syntheses*, Academic Press, NY, 1979 and M. Freifelder, *Catalytic Hydrogenation in Organic Synthesis Procedures and Commentary*, John Wiley & Sons, NY, 1978. For example, substituent groups resistant to these hydrogenation reaction conditions include such halogens as fluorine and chlorine; straight chain, branched and cyclicalkyl groups; straight chain and branched alkoxy groups; aryloxy groups such as phenoxy; carboxylic acid groups; cyano groups; and aryl groups and alkylaryl groups such as 4-methylbenzyl or 4-ethylpyridinyl.

The term "alkyl", used either alone or in compound words such as "alkylaryl" includes straight-chain or branched alkyl, such as methyl, ethyl, propyl, i-propyl, or the different butyl, pentyl or hexyl isomers. "Alkoxy" includes, for example, methoxy, ethoxy, propyloxy, isopropyloxy and the different butoxy, pentoxy and hexyloxy isomers.

The term "halogen", either alone or in compound words such as "haloalkyl", includes fluorine, chlorine, bromine or iodine, with fluorine and chlorine preferred for the process of this invention.

Preferred aryl sulfonyl chlorides include substituted and unsubstituted dimethylbenzenesulfonyl chlorides, benzenesulfonyl chlorides, pyridinesulfonyl chlorides, and naphthalenesulfonyl chlorides. Representative examples of such aryl sulfonyl chlorides include 2,5-dimethylbenzenesulfonyl chloride, 4-methylbenzenesulfonyl chloride, 2,5-bis(1-methylethyl)benzenesulfonyl chloride, 4-(chlorosulfonyl)benzoic acid, 2-methyl-4-pyridinesulfonyl chloride, 2,3-dihydro-4-thiazolesulfonyl chloride, 1-naphthalenesulfonyl chloride and 1,5-napthyridine-7-sulfonyl chloride.

Suitable solvents for use in the present invention include aprotic and protic solvents in which the reactants and products are soluble and which are resistant to the hydrogenation conditions. Aprotic solvents are preferred and include aromatic solvents such as methylbenzene, dimethylbenzene, and chlorobenzenes; tetrahydrofuran; N,N-dimethylformamide; and mixtures of one or more aprotic solvents. Protic solvents including alcohols such as isopropanol and ethanol are less preferred due to potential extra steps that may be needed to separate out the resultant chloride salt. If the sulfonyl chloride substrate is soluble in aliphatic hydrocarbons, such as hexane, heptane and octane, these solvents can be used.

The catalyst employed in the present invention comprises palladium and can be a commercial palladium catalyst on a carrier, preferably a carrier having a high specific surface area. Such carriers include for example, activated charcoal or carbon, silica gel, alumina or magnesia. The active portion of the catalyst can contain palladium alone, or it can further comprise other materials to enhance performance. A palladium catalyst further comprising tin from about 15% to about 20% the weight of the palladium is preferred. (This means, for example, if 1000 mg of palladium is present then the amount of tin ranges from about 150 mg to about 200 mg.) More preferably, the tin content is from about 8% to about 12% of the weight of the palladium. In the process of the present invention, it is preferable to use about 1 to about 3 millimoles of palladium per mole of aryl sulfonyl chloride.

The base employed in the present process for the purpose of neutralizing the hydrogen chloride produced by the reaction to a chloride salt is a relatively strong base, e.g., one whose conjugate acid has a $pK_a$ of about 2 or greater, with bases preferred whose conjugate acid has a $pK_a$ of 3 or greater. Weaker bases may not adequately neutralize the hydrogen chloride to minimize its corrosive tendencies. Any ionic base soluble in water and having the above alkalinity, and which does not harm catalyst activity, can be used. By ionic base is meant a base comprising an alkali or alkaline earth metal cation and an anion formable by dissociation of weak acid, i.e., an acid with a $pK_a$ of about 2 or greater. Preferred alkali and alkaline earth metal cations are $Li^+$, $Na^+$, $K^+$, $Ca^{2+}$ and $Sr^{2+}$, with $Na^+$ and $K^+$ most preferred. Preferred anions in the ionic bases useful for the process of this invention include acetate, carbonate and hydroxide. Ionic bases such as sodium acetate, sodium hydroxide, potassium hydroxide, sodium carbonate, and potassium carbonate are preferred. Also useful as bases for the reaction of this invention are tertiary amines that are soluble in the aprotic or protic solvent used for the reaction, excluding tertiary amines having a methyl group attached to the amine nitrogen. While not wishing to be bound by any particular theory, it is believed that tertiary amines having methyl groups attached to the amine nitrogen, such as N,N-dimethylbenzeneamine, are insufficiently sterically hindered to prevent interference with the catalyst. Preferably the tertiary amine is selected from the group consisting of alkyl aryl and arylalkyl tertiary amines. Preferred tertiary amines include N,N-diethylbenzeneamine, tributylamine, 1-ethylpiperidine and triethylamine.

The amount of base used in the reaction is preferably at least one molar equivalent to about 1.3 molar equivalents relative to the moles of sulfonyl chloride so as to neutralize all hydrogen chloride formed. Amounts larger than 1.3 molar equivalents may decrease the amount of thiol selectivity by leading to the formation of a sulfinic acid salt at the expense of the desired thiol product.

The temperature of the hydrogenation is preferably between about 20° C. and about 110° C. Lower temperatures are possible but would require special cooling equipment. Higher temperatures can cause deactivation of the catalyst and can interfere with the reaction because of poor stability of aryl thiols at high temperatures. Conducting the hydrogenation first at lower temperatures and then at higher temperatures may provide better results than conducting the hydrogenation at a single temperature. For example, an initial period of hydrogenation can be conducted at a lower temperature in the above range, e.g., at about 20° C. to about 85° C., followed by a final period of hydrogenation conducted at a higher temperature in the range, e.g., at about 85° C. to about 110° C. In the embodiment in which two periods of increasing temperature are used, the addition of hydrogen is monitored during the initial period and when hydrogen uptake ceases at this lower temperature, the temperature is raised within the range indicated above for the final period.

Upon cessation of hydrogen uptake at the higher temperature, the reaction is complete.

Alternatively, the entire period of hydrogenation can be conducted at about the same temperature.

The pressure for the hydrogenation is preferably between about 700 and 7000 kPa. Below this pressure the hydrogenation can be generally too slow for practical use. Above this pressure more expensive reaction equipment may be required.

EXAMPLES

Example 1

A one-liter Hastelloy® C-276 autoclave was charged with a methylbenzene solution of 2,5-dimethylbenzenesulfonyl chloride (400 g solution, 20.9 wt %, 0.41 mol), 5% Pd-0.5% Sn on carbon catalyst (2.0 g, 0.94 mmol Pd), and of N,N-diethylbenzeneamine (70.6 g, 0.47 mol; a 1.15 molar equivalent ratio to the sulfonyl chloride). The solution was charged with hydrogen to a pressure of 800 psig (5520 kPa) and heated to 100° C. The absorption of hydrogen stopped in 1.5 hours. The pressure was released and the solution was transferred to a beaker where 300 grams of water was added, and the mixture was stirred for 0.5 hours. The supported catalyst was filtered off and the organic and aqueous phases were separated. Analysis by gas chromatography indicated a 100% conversion of the sulfonyl chloride, a 73.1% selectivity to the corresponding thiol (2,5-dimethylbenzenethiol), and a 12.3% selectivity to the corresponding sulfonic acid (2,5-dimethylbenzenesulfonic acid). Analysis of the aqueous layer indicated 723 ppm nickel, a measure of the corrosion of the Hastelloy® autoclave body.

This example shows that N,N-diethylbenzeneamine, a strong base, may be used to react with the byproduct hydrogen chloride when converting an aryl sulfonyl chloride to an aryl thiol by catalytic hydrogenation, with a relatively small amount of corrosion.

Comparative Example 1

A one-liter Hastelloy® autoclave was charged and the reaction carried out in the same way as Example 1, but an equivalent amount of N,N-dimethylbenzeneamine (57.0 g, 0.47 mol) was substituted for N,N-diethylbenzeneamine. The hydrogen absorption stopped in 2.75 hours. Gas chromatographic analysis indicated a 100% conversion of the sulfonyl chloride, a 1.1% selectivity to the corresponding thiol, 61.0% selectivity to the corresponding disulfide, 4.1% selectivity to the corresponding sulfonothioate, and 8.5% selectivity to the corresponding sulfonic acid. Analysis of the aqueous layer indicated 5240 ppm nickel, much higher than the preceding example.

This comparative example shows the unexpected difference in results when using the N,N-dimethylbenzeneamine, a tertiary amine with a methyl group attached to the amine nitrogen compared to N,N-diethylbenzeneamine, a base useful in the present invention.

Example 2

A one-liter Hastelloy® autoclave as in Example 1 was charged with a methylbenzene solution of 2,5-dimethylbenzenesulfonyl chloride (415 g solution, 20.8%, 0.42 mol), 5% Pd-0.5% Sn on carbon catalyst (2.0 g, 0.94 mmol Pd), and a solution of sodium acetate (72.1 g, 0.53 mol; a 1.26 molar equivalent ratio to the sulfonyl chloride) in water (250 g). The solution was charged with hydrogen to 800 psig (5520 kPa), and the absorption of hydrogen began at room temperature. The solution was allowed to absorb hydrogen for 4 hours until absorption stopped. The reaction mixture was then heated to 100° C. while maintaining the hydrogen pressure at 800 psig (5520 kPa). The hydrogen pressure was maintained for 4 additional hours, at which time hydrogen absorption ceased. The pressure was then released. The supported catalyst was filtered off and the organic and aqueous phases were separated. Analysis by gas chromatography indicated a 100% conversion of the corresponding sulfonyl chloride, a 92.5% selectivity to the corresponding thiol, 0.2% selectivity to the corresponding disulfide, and 7.0% selectivity to the corresponding sulfonic acid. Analysis of the aqueous layer indicated 35 ppm nickel, showing a very low corrosion rate of the Hastelloy® autoclave.

This example shows that strong ionic bases can be used to react with the hydrogen chloride, and that excellent results are obtained when the hydrogenation is carried out in two stages, at low initial temperature followed by a higher temperature.

The following tables show the effect of other bases and/or reaction conditions. In these tables, the reaction time listed is the time in hours during which active absorption of hydrogen was in progress, after which the reaction was halted. The reaction results are shown for sulfonyl chloride conversion (shown as "Conv. %"), selectivity to the thiol (shown as "Select. % Thiol"), selectivity to the disulfide (shown as "Select. % Disulf."), and selectivity to the sulfonic acid (shown as "Select. % Sulf. Ac."). Also shown is the parts per million (ppm) of nickel (Ni) found in the aqueous phase after its separation from the organic phase, a measure of the corrosion of the (nickel-based) Hastelloy® autoclave.

Example 3

The following experiments with various amines as shown in Table 1 were carried out in essentially the same manner as Example 1 (a molar equivalent ratio to the sulfonyl chloride of about 1.15), except as noted.

TABLE 1

Comparison of Various Amine Bases on Thiol Selectivity

| Base Used | Reaction Time (h) | Conv. % | Select. % Thiol | Select. % Disulf. | Select. % Sulf. Ac. | Ni ppm |
|---|---|---|---|---|---|---|
| (Comparative Examples) | | | | | | |
| 1-Methylpiperidine | 2.5 | 100 | 17.6 | 32.1 | 16.7 | 5240 |
| N,N-Dimethylacetamide | 4.25* | 100 | 86 | 0 | ** | 64200 |
| (Examples) | | | | | | |

TABLE 1-continued

Comparison of Various Amine Bases on Thiol Selectivity

| Base Used | Reaction Time (h) | Conv. % | Select. % Thiol | Select. % Disulf. | Select. % Sulf. Ac. | Ni ppm |
|---|---|---|---|---|---|---|
| Tributylamine | 3 | 100 | 68.3 | 0.5 | 2.0 | 2900 |
| 1-Ethylpiperidine | 1 | 100 | 70.7 | 0 | 12.4 | 1190 |
| Triethylamine | 4 | 100 | 60.6 | 0 | 12.9 | 5650 |

*Reaction temperature was 90° C. rather than 100° C.
**No data collected.

The above examples show that an amine having a methyl group attached to the nitrogen, such as 1-methylpiperidine is unsatisfactory in thiol selectivity, and that N,N-dimethylacetamide is ineffective in preventing corrosion of the Hastelloy® autoclave, when compared to the non-methyl amines useful in the present invention.

Example 4

The following experiments with various ionic bases as shown in Table 2 were carried out in essentially the same manner as Example 2 (a molar equivalent ratio to the sulfonyl chloride of about 1.26), except as noted.

TABLE 2

Comparison of Various Ionic Bases on Thiol Selectivity

| Base Used | Reaction time (h) at temperature | Conv. % | Select. % Thiol | Select. % Disulf. | Select. % Sulf. Ac. | Ni ppm |
|---|---|---|---|---|---|---|
| Sodium Hydroxide | 1.5 at 30° C. 2.0 at 100° C. | 100 | 85.4 | 0.4 | 4.3 | 305 |
| Sodium Hydroxide | 3.0 at 100° C. | 100 | 68.3 | 0.4 | 4.8 | ** |
| Potassium Carbonate* | 5.8 at 30° C. 7.0 at 100° C. | 100 | 76.2 | 0.4 | 7.6 | 1 |

*0.27 moles used: a molar equivalent corresponding to 0.54 moles of a salt of a monovalent acid, and a molar equivalent ratio to the aryl sulfonyl chloride of about 1.29.
**No data collected.

The above examples show the excellent selectivity and corrosion results obtained with ionic bases of the present invention, and the improvement in results with sodium hydroxide when carrying out the initial period of the hydrogenation at a lower temperature than the final period.

TABLE 3

Effect of Pd Catalyst on Thiol Selectivity

| Base Used | Reaction time (h) at temperature | Conv. % | Select. % Thiol | Select. % Disulf. | Select. % Sulf. Ac. | Ni ppm |
|---|---|---|---|---|---|---|
| Sodium Acetate | 6 at 30° C. 8 at 100 ° C. | 100 | 81.2 | 0.4 | 4.5 | 62 |

Example 5

The following experiment shown in Table 3 was carried out in essentially the same manner as Example 2 (a molar equivalent ratio to the sulfonyl chloride of about 1.26), except that 5% Pd on carbon catalyst was used instead of 5% Pd-0.5% Sn on carbon catalyst.

The above experiment shows that excellent results can be obtained with catalyst containing supported palladium alone.

Example 6

The following experiment shown in Table 4 was carried out in essentially the same manner as Example 2 (a molar equivalent ratio to the sulfonyl chloride of about 1.26), except that 400 psig (2760 kPa) hydrogen pressure was used instead of 800 psig (5520 kPa).

TABLE 4

Effect of Hydrogen Pressure on Thiol Selectivity

| Base Used | Reaction time (h) at temperature | Conv. % | Select. % Thiol | Select. % Disulf. | Select. % Sulf. Ac. | Ni ppm |
|---|---|---|---|---|---|---|
| Sodium Acetate | 4.3 at 30° C. 8.0 at 100° C. | 100 | 69.0 | 7.6 | 12.9 | 593 |

The above example shows that, at 400 psig (2760 kPa) pressure, the thiol selectivity is poorer and corrosion higher than the results shown at 800 psig (5520 kPa) (Example 2)

Example 7

The following experiments shown in Table 5 were carried out in essentially the same manner as Example 2, except that an increased amount of base was used (a molar equivalent ratio to the aryl sulfonyl chloride of about 1.8 and 3, respectively, instead of 1.26).

TABLE 5

Effect of Base Amount on Thiol Selectivity

| Base Used | Reaction time (h) at temperature | Conv. % | Select. % Thiol | Select. % Disulf. | Select. % Sulf. Ac. | Ni ppm |
|---|---|---|---|---|---|---|
| Sodium Hydroxide* | 1.3 at 30° C. 3.0 at 100° C. | 100 | 11.0 | 17.0 | 7.9 | 11 |
| Potassium Carbonate** | 1.3 at 30° C. 1.0 at 100° C. | 100 | 0.0 | 29.0 | *** | 0 |

*(0.75 mole used: a molar equivalent ratio to the aryl sulfonyl chloride of about 1.8.
**0.62 moles used: a molar equivalent corresponding to 1.24 moles of a salt of a monovalent acid, and a molar equivalent ratio to the aryl sulfonyl chloride of about 3.
***No data collected.

The above examples show that relative to the results listed in Table 2 of Example 4 an increased amount of base can have a detrimental effect of thiol selectivity, resulting in lower yields.

What is claimed is:

1. A process for the production of an aryl thiol, comprising: hydrogenating an aryl sulfonyl chloride with hydrogen in a solvent in the presence of (i) a catalyst comprising palladium and about 5% to about 20% by weight of tin relative to the palladium and (ii) an effective amount of a base whose conjugate acid has a $pK_a$ of about 2 or greater, wherein the base is selected from the group consisting of ionic bases soluble in water and tertiary amines soluble in the solvent, the tertiary amines not having a methyl group attached to the amine nitrogen.

2. A process for the production of an aryl thiol, comprising: hydrogenating an aryl sulfonyl chloride with hydrogen in a solvent in the presence of (i) a catalyst comprising palladium and (ii) an effective amount of a base selected from the group consisting of sodium acetate, sodium hydroxide, potassium hydroxide, sodium carbonate and potassium carbonate.

3. A process for the production of an aryl thiol, comprising: hydrogenating an aryl sulfonyl chloride with hydrogen in a solvent in the presence of (i) a catalyst comprising palladium and (ii) an effective amount of a base whose conjugate acid has a $pK_a$ of about 2 or greater, wherein the base is selected from the group consisting of ionic bases soluble in water which comprise an alkali or alkaline earth metal, and tertiary amines soluble in the solvent, the tertiary amines not having a methyl group attached to the amine nitrogen.

4. The process of claims 1, 2 or 3 wherein the hydrogenation is conducted at a temperature of about 20° C. to about 110° C. and at a pressure of about 700 kPa to 7000 kPa.

5. The process of claims 1, 2 or 3 wherein the hydrogenation is initially carried out at a temperature of about 20° C. to about 85° C. followed by a temperature of about 85° C. to about 110° C.

6. The process of claims 1, 2 or 3 wherein about 1 to about 3 millimoles of palladium per mole of aryl sulfonyl chloride is used.

7. The process of claims 2 or 3 wherein the palladium catalyst further comprises from about 5% to about 20% by weight of tin relative to the palladium.

8. The process of claim 7 wherein the amount of tin is from about 8% to about 12% of the weight of the palladium.

9. The process of claims 1 or 3 wherein the base has a conjugate acid having a $pK_a$ of about 3 or greater.

10. The process of claims 1, 2 or 3 wherein the amount of base used is at least one molar equivalent to about 1.3 molar equivalents relative to the moles of aryl sulfonyl chloride.

11. The process of claims 1 or 3 wherein the tertiary amine is selected from the group consisting of alkyl, aryl and arylalkyl tertiary amines.

12. The process of claim 11 wherein the tertiary amine is selected from the group consisting of N,N-diethylbenzeneamine, tributylamine, 1-ethylpiperidine, and triethylamine.

13. The process of claims 1, 2 or 3 wherein the aryl sulfonyl chloride is selected from the group consisting of substituted and unsubstituted methylbenzenesulfonyl chlorides, benzenesulfonyl chlorides, pyridinesulfonyl chlorides, thiazolesulfonyl chlorides, oxazolesulfonyl chlorides, naphthalenesulfonyl chlorides, benzothiophene-sulfonyl chlorides, and benzofuransulfonyl chlorides, and benzofuransulfonyl chlorides.

14. The process of claims 1, 2 or 3 wherein the solvent is aprotic.

15. The process of claim 1 wherein the amount of tin is from about 8% to about 12% of the weight of the palladium.

* * * * *